US007622129B1

(12) United States Patent
Haberstroh et al.

(10) Patent No.: US 7,622,129 B1
(45) Date of Patent: Nov. 24, 2009

(54) NANO-STRUCTURED POLYMERS FOR USE AS IMPLANTS

(75) Inventors: Karen M. Haberstroh, Lafayette, IN (US); Thomas J. Webster, Lafayette, IN (US); Anil Thapa, Pittsburgh, PA (US); Derick C. Miller, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 505 days.

(21) Appl. No.: 10/634,292

(22) Filed: Aug. 5, 2003

Related U.S. Application Data

(60) Provisional application No. 60/401,060, filed on Aug. 5, 2002.

(51) Int. Cl.
*A61K 9/00* (2006.01)
*C12N 5/00* (2006.01)
*C12N 5/02* (2006.01)

(52) U.S. Cl. .................. 424/400; 424/422; 435/325; 435/395

(58) Field of Classification Search ................ 424/400, 424/422; 435/325, 395
See application file for complete search history.

(56) References Cited

U.S. PATENT DOCUMENTS

| | | | |
|---|---|---|---|
| 4,776,853 A | 10/1988 | Klement et al. | |
| 4,795,436 A | 1/1989 | Robinson | |
| 4,902,508 A | 2/1990 | Badylak et al. | |
| 4,998,239 A | 3/1991 | Strandjord et al. | |
| 5,281,422 A | 1/1994 | Badylak et al. | |
| 5,292,328 A | 3/1994 | Hain et al. | |
| 5,306,311 A | 4/1994 | Stone et al. | |
| 5,372,821 A | 12/1994 | Badylak et al. | |
| 5,415,704 A | 5/1995 | Davidson | |
| 5,573,784 A | 11/1996 | Badylak et al. | |
| 5,733,337 A | 3/1998 | Carr, Jr. et al. | |
| 5,744,515 A | 4/1998 | Clapper | |
| 6,106,913 A | 8/2000 | Scardino et al. | |
| 6,183,255 B1 | 2/2001 | Oshida | |
| 6,262,017 B1 | 7/2001 | Dee et al. | |
| 6,270,347 B1 | 8/2001 | Webster et al. | |
| 6,291,070 B1 | 9/2001 | Arpac et al. | |
| 6,319,264 B1 | 11/2001 | Tormala et al. | |
| 6,344,367 B1 | 2/2002 | Naya et al. | |
| 6,355,198 B1 | 3/2002 | Kim et al. | |
| 6,368,859 B1 | 4/2002 | Atala | |
| 6,396,208 B1 | 5/2002 | Oda et al. | |
| 6,572,672 B2 | 6/2003 | Yadav et al. | |
| 6,669,706 B2 | 12/2003 | Schmitt et al. | |
| 6,689,374 B2 | 2/2004 | Chu et al. | |
| 6,756,286 B1 | 6/2004 | Moriceau et al. | |
| 6,790,455 B2 | 9/2004 | Chu et al. | |
| 6,797,514 B2 | 9/2004 | Berenson et al. | |
| 6,805,898 B1 | 10/2004 | Wu et al. | |
| 6,881,249 B2 | 4/2005 | Anderson et al. | |
| 6,929,539 B2 | 8/2005 | Schutz et al. | |
| 2002/0167118 A1 | 11/2002 | Billiet et al. | |
| 2002/0173033 A1* | 11/2002 | Hammerick et al. | 435/305.2 |
| 2002/0173213 A1 | 11/2002 | Chu et al. | |
| 2003/0040809 A1 | 2/2003 | Goldmann et al. | |
| 2003/0050711 A1 | 3/2003 | Laurencin et al. | |
| 2004/0028875 A1 | 2/2004 | Van Rijn et al. | |
| 2004/0104672 A1 | 6/2004 | Shiang et al. | |
| 2004/0131753 A1 | 7/2004 | Smith et al. | |
| 2004/0171323 A1 | 9/2004 | Shalaby | |
| 2004/0241211 A9 | 12/2004 | Fischell et al. | |
| 2006/0173471 A1 | 8/2006 | Carr, Jr. et al. | |

FOREIGN PATENT DOCUMENTS

| | | |
|---|---|---|
| WO | WO 97/25999 | 7/1997 |
| WO | WO 01/55473 | 8/2001 |
| WO | WO 03/015836 | 2/2003 |

OTHER PUBLICATIONS

U.S. Appl. No. 10/362,148.*
U.S. Appl. No. 10/793,721.*
Jean-Louis Pariente et al., "In vitro biocompatibility assessment of naturally derive and synthetic biomaterials using normal human urothelial cells," *J. Biomed. Mater. Res.*, 55(1), (2001), pp. 33-39.
Malachy J. Gleeson et al., "The use of alloplastic biomaterials in bladder substitution," *J. Urol.*, 148, (1992), pp. 1377-1382.
Janeta Nikolovski et al., Smooth muscle cell adhesion to tissue engineering scaffolds, *Biomat.*, 21, (2000), pp. 2025-2032.
Anthony Atala et al., "Implantation in vivo and retrieval of artificial structures consisting of rabbit and human urothelium and human bladder muscle," *J. Urol.*, 150, (1993), pp. 608-612.
M. J. Lyndon et al., "Cellular interactions with synthetic polymer surfaces in culture," *Biomat.* 6, (1985), pp. 396-402.
A. S. G. Curtis et al., "Adhesion of cells to polystyrene surfaces," *J. Cell Biol.*, 97, (1983), pp. 1500-1506.
Joseph A. Chinn et al., "Enhancement of serum fibronectin adsorption and the clonal plating efficiencies of Swiss mouse 3T3 fibroblast and MM14 mouse myoblast cells on polymer substrates modified by radiofrequency plasma deposition," *J. Colloid Interface Sci.*, 127, (1989), pp. 67-87.
Paul Goldhaber, "The influence of pore size on carcinogenicity of subcutaneously implanted Millipore filters," *Proc. Am. Assoc. Cancer Res.*, 3 (1961), p. 28.
J. Brauker et al., "Neovascularization of immunoisolation membranes: the effect of membrane architecture and encapsulated tissue," *Transplant Proc.*, 24, (1992); p. 2924.

(Continued)

*Primary Examiner*—Ruth A Davis
(74) *Attorney, Agent, or Firm*—Barnes & Thornburg LLP (57) ABSTRACT

Polymeric materials and processes for making the same are provided herein wherein said polymeric materials have nano-sized topological features or textures. These features have dimensions in various ranges including, but not limited to, dimensions less than about 100 nanometers. In addition, polymeric materials are described herein that have a surface roughness of about 50 nm or greater. These polymeric materials are useful for making implants for soft tissues, such as bladder tissue replacement implants. Methods of treatment using such implants are also described. In such methods, polymers that are biocompatible, and biodegradable are also described.

28 Claims, 1 Drawing Sheet

OTHER PUBLICATIONS

Paul Weiss, "In vitro experiments on the factors determining the course of the outgoing nerve fiber," *J. Exp. Zool.*, 68, (1945), pp. 393-448.

G. A. Dunn et al., "Alignment of fibroblasts on grooved surfaces described by a simple geometric transformation," *J. Cell Sci,*, 83, (1986), pp. 313-340.

J. Meyle et al., "Variation in contact guidance by human cells on a microstructured surface," *J. Biomed. Mater. Res.*, 29, (1995), pp. 81-88.

John A. Schmidt et al., "Macrophage response to microtextured silicone," *Biomat.*, 12, (1992), pp. 385-389.

Karen M. Haberstroh et al., "The effects of sustained hydrostatic pressure on select bladder smooth muscle cell functions," *J. Urol.*, 162, (1999), pp. 2114-2118.

Jinming Gao et al., "Surface hydrolysis of poly(glycolic acid) meshes increases the seeding density of vascular smooth muscle cells," *J. Biomed. Mat. Res.*, 42, (1998), pp. 417-424.

Mark A. Schubert et al., "Role of oxygen in biodegradation of poly(etherurethane urea) elastomers," *J. Biomed. Mat. Res.*, 34, (1997), pp. 519-530.

Thomas J. Webster et al., "Osteoblast adhesion on nanophase ceramics," *Biomaterials*, 20, (1999), pp. 1221-1227.

M. Conley et al., "Effects of biodegradable polymer particles on rat marrow-derived stromal osteoblasts in vitro," *Biomaterials*, 19, (1998), pp. 1255-1268.

Susan L. Ishaug-Riley et al., "Three-dimensional culture of rat calvarial osteoblasts in porous biodegradable polymers," *Biomaterials* 19, (1998), pp. 1405-1412.

Susan L. Ishaug-Riley et al., "Human articular chondrocyte adhesion and proliferation on synthetic biodegradable polymer films," *Biomaterials*, 20, (1999), pp. 2245-2256.

Laurence S. Baskin et al., "Cellular Signaling in the Bladder," www.bioscience.org., *Frontiers in Bioscience*, 2, d592-595, (1997), 8 pgs.

Gunilla Dahlfors et al., "Vascular Endothelial Growth Factor and Transforming Growth Factor-β1 Regulate the Expression of Insulin-Like Growth Factor-Binding Protein-3, -4, and -5 in Large Vessel Endothelial Cells," *The Endocrinology Society*, vol. 141, No. 6, (2000), pp. 2062-2067.

Jinming Gao et al., "Surface hydrolysis of poly(glycolic acid) meshes increases the seeding density of vascular smooth muscle cells," *J. Biomed Mater Res*, 42, (1998), pp. 417-424.

Karen M. Haberstroh et al., "The Effects of Sustained Hydrostatic Pressure on Select Bladder Smooth Muscle Cell Functions," *The Journal of Urology*, vol. 162, (1999), pp. 2114-2118.

Antonios G. Mikos et al., "Preparation and Characterization of poly(L-lactic acid) foams," *Polymer*, vol. 35, No. 5, (1994), pp. 1068-1077.

Kenjiro Yamakawa et al., "Peroxisome Proliferator-Activated Receptor-γ Agonists Increase Vascular Endothelial Growth Factor Expression in Human Vascular Smooth Muscle Cells," *Biochemical and Biophysical Research Communications*, 271, (2000), pp. 571-574.

Young-Jo Kim et al., "Fluorometric Assay of DNA in Cartilage Explants Using Hoechst 33258," *Analytical Biochemistry*, 174, (1988), pp. 168-176.

Kari I. Kivirikko et al., "Modifications of a Specific Assay for Hydroxyproline in Urine," *Analytical Biochemistry*, 19, (1967), pp. 249-255.

C. B. Wilson et al., "Extracellular matrix and integrin composition of the normal bladder wall," *World J Urol.* 14, (1996), pp. S30-S37.

Paul Weiss, "Experiments on Cell and Axon Orientation in Vitro: The Role of Colloidal Exudates in Tissue Organization," Journal of Experimental Zoology, vol. 100(3), (1943), pp. 353-386.

J. Black and G. Hastings, "Handbook of Biomaterial Properties", *Chapman & Hall*, pp. 40-47 (1998).

Mankin et al., "Orthopaedic Basic Science—Chapter 1 Form and Function of Articular Cartilage", *American Academy of Orthopaedic Surgeons*, pp. 1-45, (1994).

Kay et al., "Nanostructured Polymer/Nanophase Ceramic Composites Enhance Osteoblast and Chondrocyte Adhesion", *Tissue Engineering*, vol. 8, No. 5, pp. 753-761, (2002).

Thapa et al., "An Investigation of Nano-structured Polymers for Use as Bladder Tissue Replacement Constructs", *Mat. Res. Soc. Symp. Proc.*, vol. 711, pp. 205-210, (2002).

Miller et al., An In Vitro Study of Nano-fiber Polymers for Guided Vascular Regeneration, *Mat. Res. Soc. Symp. Proc.*, vol. 711, pp. 201-204, (2002).

Jun et al., "An In Vitro Study of Chondrocyte Function on Nanostructured Polymer/Ceramic Formulations to Improve Cartilage Repair", *Nano 2002* Conference Abstract Book, Orlando, FL, p. 269, (2002).

Tepper et al., "Nanosized alumina fibers," *American Ceramic Society Bulletin*, 80(6):57-60 (2001).

Webster et al., "An in vitro evaluation of nanophase alumina for orthopaedic/dental applications," *Bioceramics Volume 11 (Proceedings of the 11th International Symposium on Ceramics in Medicine)*, 273-76 (LeGeros & LeGeros eds., World Scientific Publishing Co, 1998).

Webster et al., "Hydroxylapatite with substituted magnesium, zinc, cadmium, and yttrium. II. Mechanisms of osteoblast adhesion," *J. Biomed. Mater. Res.*, 59:312-17 (2002).

Dee et al., "Design and function of novel osteoblast-adhesive peptides for chemical modification of biomaterials," *J. Biomed. Mater. Res.*, 40:371-77 (1998).

Webster et al., "Specific proteins mediate enhanced osteoblast adhesion on nanophase ceramics," *J. Biomed. Mater. Res.*, 51:475-83 (2000).

Webster et al., "Enhanced functions of osteoblasts on nanophase ceramics," *Biomaterials*, 21:1803-10 (2000).

Curtis & Wilkinson, "Review. Topographical control of cells," *Biomaterials*, 18(24):1573-83 (1997).

Puleo & Bizios, "RGDS tetrapeptide binds to osteoblasts and inhibits fibronectin-mediated adhesion," *Bone*, 12:271-76 (1991).

Siegel, "Creating nanophase materials," *Scientific American*, 275(6):74 (1996).

Webster et al., "Design and evaluation of nanophase alumina for orthopaedic/dental applications," *Nanostructured Materials*, 12:983-86 (1999).

Webster et al., "Enhanced surface and mechanical properties of nanophase ceramics to achieve orthopaedic/dental implant efficacy," *Key Engineering Materials*, vols. 192-195, pp. 321-324 (Proceedings of the 13th international symposium on ceramics in medicine, Bologna, Italy, 2000 (Trans Tech Publications, 2001).

Webster et al., "Mechanisms of enhanced osteoblast adhesion on nanophase alumina involve vitronectin," *Tissue Engineering*, 7(3):291-301 (2001).

Webster et al., "Nanoceramic surface roughness enhances osteoblast and osteoclast functions for improved orthopaedic/dental implant efficacy," *Scripta Mater.*, 44:1639-42 (2001).

Office Action for U.S. Appl. No. 10/362,148, US Patent & Trademark Office, May 27, 2009.

\* cited by examiner

NANO-STRUCTURED POLYMERS FOR USE AS IMPLANTS

CROSS-REFERENCE TO RELATED APPLICATIONS

The present application claims the benefit of provisional patent application Ser. No. 60/401,060, entitled "Investigation of Nano-Structured Polymers for Use as Bladder Tissue Constructs," filed on Aug. 5, 2002, the entire description of which is incorporated herein by reference. Cross reference is made to international application Ser. No. PCT/US02/25812, filed Aug. 14, 2002, which claims the benefit of provisional patent application Ser. No. 60/312,800, filed Aug. 16, 2001.

This work was supported in part by National Science Foundation Grant No. 9972770-DGE. The government may have certain rights in this invention.

FIELD

The invention relates to synthetic implants. In particular, a synthetic implant suitable for soft tissue reconstruction is described.

BACKGROUND

Methods of reconstructing soft tissues are needed for patients that suffer from disease states that implicate those tissues, or patients who have undergone surgery, including surgery to correct certain disease states.

For example, approximately 400 million people worldwide were reportedly affected by bladder disease by the end of 1999. One of the common forms of bladder cancer is urinary bladder cancer. This cancer is also a common malignancy of the genitourinary tract and a leading cause of cancer among American men. Many forms of bladder cancer are superficial. In the majority of these cases, a suitable treatment involves local resection of the cancerous portion of the bladder wall combined with adjuvant intravesical immuno-chemotherapy. However, in cases where this treatment regimen is unsuccessful, and in cases where the bladder cancer is not superficial, treatment often involves cystectomy of a portion of, or of the entire, bladder wall. This procedure is performed in order to stop the progression of the disease and to reduce mortality. Following such resection procedures, the bladder can be reconstructed using implants.

The bladder is a musculomembraneous sac that acts as a reservoir for urine. The bladder is constructed from two main parts: (a) the body, which is the major part of the bladder and the portion in which urine collects; and (b) the neck, which is a funnel-shaped extension of the body, passing into the urogenital triangle (trigone), and connecting with the lower bladder opening (urethra). Two ureters, originating at the kidneys, enter the bladder at the uppermost angles of the trigone. An empty bladder has the form of a flattened tetrahedron, with its vertex tilted forward, thus presenting structures such as a fundus, a vertex, and superior and interior surfaces. A full bladder contains about 0.5 liters (L) of fluid and assumes an oval form, the long diameter of which is about 12 cm in length.

Bladder tissue is composed of four coats, a serous, a mucous, a submucous, and a muscular coat. Each of these coats is also associated with an extracellular matrix. The serous coat is a very thin layer derived from the peritoneum, a transparent membrane that lines the abdominal cavity in mammals. It develops the superior surface and the upper parts of the lateral surfaces of the bladder wall. The mucous coat is thin and smooth, and has a loose texture allowing it to be arranged in folds when the bladder is empty. However, over the trigone, the mucous membrane is formed from different-shaped urothelial cells that can accommodate both the distended and the contracted bladder. The submucous coat is formed from a layer of interstitial tissue, which is closely attached to the mucous coat and connects it to the muscular coat. The muscular coat is the major component of the bladder wall and is formed from three layers muscular fibers, an external layer, a middle layer, and an inner layer.

The external layer of muscular fibers has a longitudinal arrangement. These fibers are thick as compared to the other layers in the muscular coat of the bladder wall. The middle layer of muscular fibers has a circular arrangement. These fibers are generally thin, and scattered irregularly over the body of the bladder. The inner layer of muscular fibers, that next to the submucous coat, has a general longitudinal arrangement, and are also arranged in a thin manner.

It is desirable that the material from which implants are constructed or fabricated exhibit similar material and mechanical properties to the native tissue being replaced or reinforced. Accordingly, materials that mimic soft tissues, such as bladder tissue described herein, are desirable.

SUMMARY

Polymeric materials having sub-micron sized or nano-sized topographical or topological features or textures are described herein. These features have dimensions in various ranges including, but not limited to dimensions less than about 1 micrometer, ranges from about 100 nm to about micrometer, dimensions of about 100 nm or less, ranges from about 50 nm to about 100 nm, dimensions of about 50 nm or less, and ranges from about 25 nm to about 50 nm. Such polymeric materials also include topographical or topological features or textures that exhibit surface roughness of about 50 nm or greater, about 100 nm or greater, and of about 200 nm or greater.

Examples of polymeric materials capable of exhibiting such topographical features or textures include materials comprising polymers such as, but not limited to polyglycolic acid (PGA), polylactic acid (PLA), poly(lactic acid-glycolic acid) (PLGA), poly(ether-urethane) (PU), polycaprolactone (PCL), poly(glycolide-caprolactone), and the like. Sub-micron sized or nano-sized surface features may be formed by chemical treatment processes, using acidic, basic, oxidizing, and reducing agents, as described herein. Sub-micron sized or nano-sized surface features may also be formed using molding processes, as described herein, or a combination of molding and chemical treatment processes.

Chemical treatment processes include treatment with acids, bases, oxidizing agents, and or reducing agents. Acids useful for these processes include, but are not limited to HCl, $H_2SO_4$, $HClO_4$, $HNO_3$, $H_3PO_4$, HF, and the like. Bases useful for these processes include, but are not limited to NaOH, $K_2CO_3$, $NaHCO_3$, and the like.

Methods for repairing soft tissues, including but not limited to the bladder, in patients suffering from an injury or as a result of a surgical procedure are described herein. Such methods use the polymers and implants described herein. Implants and polymers described herein may optionally include additional components including, but not limited to populations of cells; extracellular matrix components, including but not limited to proteins such as collagens I, III, IV, and V, vitronectin, laminin, fibronectin, elastin, elastin-associated microfibrillar proteins, proteoglycans, and the like; and other medically or surgically useful substances that may facilitate the repair process.

DETAILED DESCRIPTION

In one embodiment, an implant is described herein that is formed from a polymer having sub-micron sized or nano-sized surface features. In one aspect, implants described herein are suitable for use as repair components for soft tissues, such as the bladder.

In one illustrative aspect of the implants described herein, the implants facilitate and/or enhance the adhesion and or proliferation of bladder smooth muscle cells onto the surface of the implant. Without being bound by theory, it is appreciated that implants having nano-structured surfaces, or the presence of surface features having dimensions in the nanometer range may account for the facilitation, or enhancement of cell adhesion, and or cell proliferation described herein.

In another embodiment, the implants described herein include implants that possess appropriate topographical and surface chemistry properties for use as repair components for soft tissues, such as the bladder. Such topographical and surface chemistry properties can be analyzed by any of several analytical techniques including, but not limited to scanning electron microscopy (SEM), atomic force microscopy (AFM), electron spectroscopy for chemical analysis (ESCA), and the like.

In one illustrative aspect, the polymeric materials used to fabricate implants described herein are polymeric materials that include textures or features on their surfaces that have at least one dimension in the nanometer range or sub-micron range. In one aspect, the textures and or surface features on the surface of the polymeric materials described herein illustratively have dimensions less than about 1 micrometer, or in the range from about 100 nm to about micrometer. In another aspect, the textures and or surface features on the surface of the polymers described herein illustratively have dimensions less than about 100 nm, or in the range from about 50 nm to about 100 nm, or less than about 50 nm, or in the range from about 25 nm to about 50 nm.

As used herein, the term "dimensions" refers the various measurements of lines, planes, and surfaces that form at least a part of the texture and or surface features present on polymers described herein. Such dimensions include measurements internal to a surface feature, such as a peak heights, or peak widths at half-height, and the like, or the corresponding measurement applied to a valley. Dimensions internal to three-dimensional features are also included, such as the diameter or circumference of a circle inscribed in a peak, or the corresponding measurement applied to a valley. These dimensions in combination describe the surface features. It is appreciated that such dimensional measurements are dependent upon the nature of the surface features. For example, peaks may be defined by dimensions taken from or referenced to other features, such as an adjacent plane or plateau, an adjacent valley, or a midline or other reference line through adjacent peaks or peak half heights. Further, ridges may be defined by dimensions relating to pitch, thickness, and the like. Surface features include structures such as, but not limited to grains, fibers, capsules, bumps, valleys, ridges, peaks, grooves, and the like.

In one illustrative aspect, the polymer materials used to fabricate implants described herein include materials having pore sizes less than about 0.6 µm. In another aspect, the fibers and or strands formed by such polymers or polymeric materials are less than about 5 µm in length. In another aspect, the surfaces of the materials display textures and or surface features such as, but not limited to grains, fibers, capsules, bumps, valleys, ridges, peaks, grooves, and the like, illustratively having dimensions from about 1 to about 8 µm, or from about 2 to about 5 µm. In another aspect, the surface features of the polymer materials illustratively have depths of about 1.2 µm, and a pitch of about 0.9 µm. In another aspect, the surfaces of the polymeric materials illustratively have peaks less than about 100 $\mu m^2$, about 25 $\mu m^2$, or about 4 $\mu m^2$. In another aspect, the peaks are uniformly displayed on the surface of the implant, or polymeric materials used in fabricating implants.

In one aspect, nano-structured surfaces, or the presence of surface features having dimensions in the nanometer range may be characterized as a nanometer surface roughness. Surface roughness may be measured and or evaluated using a variety of standard analytical techniques, including AFM. It is further appreciated that certain values of nanometer surface roughness may also increase bladder smooth muscle cell function once adhesion, and or proliferation occurs. Nano-structured surfaces described herein include surfaces that have a surface roughness greater than about 50 nm, or greater than about 100 nm. In other aspects, the nano-structured surfaces described herein have a surface roughness greater than about 200 nm.

In another embodiment, the implants and polymeric materials described herein include those that display on their surface certain percentages of elemental composition, such as carbon, hydrogen, or oxygen; or certain percentages of chemical functional groups, such as hydroxyl, carbonyl, carboxamido, or carboxylate groups. Chemical treatment processes are described herein may also be used to alter the percentages of elemental composition, or the percentages of certain chemical functional groups prior to treatments, and illustratively to values that differ from those exhibited by conventional polymeric materials.

In one aspect, the surfaces of the implants described herein include implants having varying levels of wettability, such as intermediate wettability. It is appreciated that both the elemental compositions and or the percentages of certain chemical functional groups, such as hydroxyl, carbonyl, carboxamido, or carboxylate groups may characterize the wettability profile of the surface. An intermediate wettability profile may enhance cell adhesion, cell proliferation, contribute to appropriate cell morphology and spreading, or enhance the fate and or function of surface-attached cells.

In one embodiment, the polymeric materials described herein include polymeric films. Such polymeric films include, but are not limited to films formed from polyglycolic acid (PGA), polylactic acid (PLA), poly(lactic acid-glycolic acid) (PLGA), poly(ether-urethane) (PU), polycaprolactone (PCL), poly(glycolide-caprolactone), and the like. It is appreciated that other synthetic materials may be modified to include nano-sized surface features, and include but are not limited to acrylic mold, polyvinyl sponge, polytetrafluoroethylene (PTFE), gelatin sponge, silicon rubber, collagen/polyglactin membrane, polydimethylsiloxane (PDMS), and the like. Such materials may also be used for fabricating implants as described herein.

In one aspect, the polymers described herein include polymeric materials that have been separately treated for a selected period of time with a reagent that is capable of modifying the surface of the material. Such modifications are illustratively chemical reactions with the polymer molecules. Any reagent that may react with a portion or portions of the polymer molecules may modify the surface in ways that create or generate sub-micron sized or nano-sized topographical or topological features or textures. For example, bases including, but not limited to NaOH, $K_2CO_3$, $NaHCO_3$, and the like may be used to modify the surfaces of polymers having functional groups susceptible to saponification reactions, including, but not limited to PLGA, PCL, and the like. Further, such reagents include acids, such as mineral acids, including, but not limited to HCl, $H_2SO_4$, $HClO_4$, $HNO_3$, $H_3PO_4$, HF, and the like. Acid-based reagents may be used to modify the surfaces of polymers having functional groups susceptible to acid-catalyzed hydrolytic reaction, such as PU, and the like. Further, reagents may include oxidizing and reducing agents that may effect chemical reactions of the polymers on the surface of the polymeric materials described herein.

In one aspect, the period of treatment is a brief treatment, such as a period in the range from about 1 minute to about 10 minutes. In another aspect, the period of treatment is of intermediate length, such as a period in the range from about 10 minutes to about 30 minutes. In another aspect, the period of treatment is a long treatment, such as a period in the range from about 30 minutes to about 90 minutes, or in the range from about 30 minutes to about 120 minutes.

Without being bound by theory, such chemical treatments may cause certain molecular bonds in the polymers on the surface of the polymeric material to break. If two bonds that are proximal to one another each break, a chain from the polymer molecule may be freed from the bulk polymeric material. It is therefore appreciated that the length of treatment is selected to give the desired amount of bond breaking of polymeric surfaces. Longer treatment times will tend to effect more bond breaking. It is further appreciated that the times are dependent upon the nature of the chemical treatment. More concentrated chemical treatments will achieve the same results in shorter times than will less concentrated chemical treatments. In addition, it is understood that depending upon the chemical reaction that is taking place, stronger reagents that effect the chemistry will require sorter treatment times than will weaker reagents. For example, if the reagent is a base, and the desired chemical reaction is a saponification, such as of a carboxylic acid function, a strong base such as NaOH, and the like, will be more effective in a shorter time than will a weak base such as $NaHCO_3$, and the like. It is further appreciated that the selection of reagents and times is also dependent upon the polymeric material.

Illustratively, polymeric materials are treated with reagents such as NaOH, $HNO_3$, and the like for a selected period of time necessary to modify the polymeric surface. Illustratively, PU is treated with $HNO_3$ for a selected period of time necessary to modify the polymeric surface, including times in the range from about 1 to about 60 minutes, such as for about 10 or about 30 minutes. Illustratively, PLGA and PCL are treated with NaOH for a selected period of time necessary to modify the polymeric surface, including times in the range from about 1 to about 120 minutes, such as about 10, about 30, or about 60 minutes. It is appreciated that such treatments may reduce the surface feature dimensions presented on polymers from those present prior to treatment. Surface dimensions prior to treatment are illustratively conventional, micron-sized dimensions. Surface dimensions following treatment are illustratively sub-micron, or nanometer-sized or nano-sized dimensions. In one aspect, the nano-sized dimensions are similar to those generally encountered in biological organisms.

In another embodiment, the implants described herein include implants and polymeric materials that have been treated with solutions of extracellular matrix components, such as but not limited to protein solutions, and the like. It is suggested that proteins for example adsorbed onto the surface of the implants and polymeric materials described herein may increase the viability of cells adhering to, migrating to, or spreading onto the surface of the implants. It is appreciated that the nano-dimensional nature of the implants and polymeric materials described herein may facilitate the binding of necessary proteins, tissues, and or other extracellular matrix components. It is further appreciated that the nano-dimensional nature of the implants and polymeric materials described herein may affect the molecular conformations or structures of such adsorbed components in a manner that mimics the natural structure of soft tissues, such as bladder tissue, and or facilitates the adherence, proliferation, and function of cells growing in and around the implant.

In another embodiment, the implants described herein include implants and polymeric materials that include extracellular matrix components. It is appreciated that these extracellular matrix components can be the same components that are found in the soft tissues. Illustrative extracellular matrix components include extracellular matrix problems such as, but not limited to collagens, including collagens I, III, IV, and V, gelatin, albumin, vitronectin, laminin, fibronectin, elastin, elastin-associated microfibrillar proteins, proteoglycans, and the like. In one illustrative aspect, the extracellular matrix components are incorporated into the implant. In another illustrative aspect, the extracellular matrix components are coated onto the surface of the implant. In another illustrative aspect, the extracellular matrix components are both incorporated into and coated onto the surface of the polymeric materials or implant.

It is appreciated that collagens I and III may be the major collagens generally found in the bladder wall. These collagens may be derived from smooth muscle cells in the muscular layer and fibroblasts in the transitional layer. It is further appreciated that type IV collagen generally surrounds individual smooth muscle cells within the muscular layers, and may be a major component of the urothelium.

It is further appreciated that elastin and elastin-associated microfibrillar proteins are generally associated with the bladder wall and may contribute to the flexibility and elasticity of the bladder wall. It is further appreciated that the local arrangement of and the interaction among these various matrix proteins and the cellular components of the bladder wall may contribute to the abilities of the bladder to expand during filling and contract during emptying.

In another embodiment, the synthetic implants described herein include synthetic implants that include a population of cells. It is appreciated that these cells can be the same cells that are found in native soft tissues. For bladder, cells such as, but not limited to smooth muscles cells, fibroblasts, urothelial cells, and the like, can be included in the implants described herein. In one aspect, the cells or the population of cells are seeded onto the implant. In one aspect, the density of cell seeding is about 190,000 cells/$mm^3$. It is appreciated that in other aspects the seeding may be at a lower density.

In another embodiment, the synthetic implants described herein include synthetic implants that have additional components that facilitate processes such as the recruitment of cells, body fluids, or proteins, wound healing, cell attachment, tissue remodeling, and the like. Such additional components include, but are not limited to proteins, such as arginine-glycine-aspartic acid (RGD) peptides; cells, such as neutrophils, monocytes, fibroblasts, and macrophages; growth factors and cytokines; and the like. It is appreciated that following the implantation of implants described herein, the patient's body may coat at least a portion of the implant with protein, fibrous tissue, and other material. Such coating processes may be the initial processes of cell and or tissue ingrowth, or may be the precursor processes to cell and or tissue ingrowth.

In another embodiment, the synthetic implants described herein include synthetic implants that have any of a variety of medically or surgically useful substances including, but not limited to antiviricides such as acyclovir, ribarivin, and interferons; antimicrobials and or antibiotics such as erythromycin, bacitracin, cephalosporins, doxycycline, clindamycin, kanamycin, metronidazole, neomycin, penicillin, polymyxin B, teracyclines, viomycin, chloromycetin, streptomycins, cefazolin, ampicillin, azactam, tobramycin, and gentamycin; amino acids and peptides; vitamins; inorganic elements; cofactors for protein synthesis; hormones; endocrine tissue or tissue fragments; synthesizers; enzymes such as collagenase, peptidase, oxidases; pain relievers such as salicylic acid, acetaminophen, ibuprofen, naproxin, piroxicam, flurbiprofen, morphine, bupivacaine, benzocaine, lidocaine and xylocaine; anti-inflammatory agents such as hydrocortisone and predinose; antiparasitic agents such as quinacrine, chloroquine, and vidarabine; and antifungal agents such as nystatin; and the like.

In another embodiment, the polymeric materials described herein include materials that are used to create molds, such as silastic molds. These molds can be further used to synthesize, prepare, or fabricate nano-structured surfaces on other polymeric materials or implants made therefrom, without chemical etching procedures. In one aspect, a polymeric material or implant is prepared having sub-micron or nano-sized structural, topological, or texture features on its surface. The preparation may include a chemical etching process, such as the chemical treatment processes described herein. However, it is appreciated that any source of polymeric material displaying or having such nano-sized features may be used in the molding processes described herein.

In another aspect, the molding processes described herein may employ other materials having nano-sized structural, topological, or textural features on their surface, from which polymeric materials may be fabricated by molding. These materials may be metallic, ceramic, materials and the like, or may be natural tissues, such as native soft tissues. Thus, the molding processes described herein do not require polymeric materials from which to prepare the polymeric materials having nano-sized structural, topological, or textural features on their surface described herein.

It is appreciated that the chemical treatment or chemical etching techniques and processes described herein that are used to fabricate nano-structured polymeric materials may also alter the surface chemistry of the treated polymers as compared to the polymers without treatment. In particular, both the elemental composition, as well as the nature and population of chemical functional groups may change. Nevertheless, it is understood that changes in the elemental and or functional group composition of the surface of the implant may not impair its ability to facilitate the ingrowth of cells and or tissues onto the implant. Moreover, in certain variegations of the processes described herein, the surface chemistry of the polymeric materials described herein may be altered in a way that improves the ability of implants fabricated therefrom to facilitate the ingrowth of cells and or tissues onto the implant.

It is also appreciated that the molding processes described herein are capable of being used to fabricate nano-structured polymeric materials without altering the surface chemistry when compared to untreated polymeric materials. It is understood that the creation of nano-sized structures without altering either the elemental and or functional group composition of the surface may facilitate processes such as cell adhesion and cell proliferation, and improved cell morphology.

In another embodiment, the implants described herein include implants that exhibit material, structural, and mechanical properties that are similar to the native tissues wherein the implants will be used. Further, the implants described herein include implants that have surface features having dimensions similar to components found in the native tissues. For example, with regard to native bladder tissue, it is appreciated that collagens, such as collagens I, II, and IV, form triple helical structures having lengths of about 300 nm, periodicities of about 67 nm, and widths of about 0.5 nm. Further, fibronectin forms a dimer of identical subunits having lengths from about 60 to about 70 nm, and widths from about 2 to about 3 mm. Further, laminin forms a cruciform configuration with one long arm of about 50 nm, and two short arms of about 35 nm, and having a total length of about 50 nm, and total width of about 70 nm. Vitronectin is a linear molecule of about 15 nm long. Polymeric materials and the implants made therefrom having surface features mimicking the foregoing shapes of such proteins are contemplated to fall within the invention described herein.

In another embodiment, the implants described herein include implants that are stable to pressures applied to the tissue construct. Illustratively, the applied pressures are about 5 to about 10 cmH$_2$O, about 50 to about 90 cmH$_2$O, or about 54 to about 82 cmH$_2$O. It is understood that this stability to the application of pressure may be relevant to the isolated implant material, and or to the implant-native tissue interface found in a repaired structure, such as the interface formed by implants described herein and bladder tissue.

In another aspect, the implants described herein include implants that are cytocompatible and biocompatible. The cytocompatibility and biocompatibility of the implants can be measured, evaluated, and or tested in vitro, using procedures described herein, such as by monitoring cell adhesion and cell proliferation on the implant materials described herein. In addition, the morphology of cells adhered to the implant materials described herein may be monitored.

In another embodiment, the implants described herein include implants that are biodegradable, bioresorbable, or bioerodable implants. It is appreciated that the conditions under which the implants are biodegraded, bioeroded, or bioresorbed can be predetermined. It is further appreciated that the polymeric materials from which such implants are made can primarily determine the conditions under which the implants are biodegraded, bioeroded, or bioresorbed. In one illustrative aspect, the biodegradation, bioresorption, or bioerosion of implants described herein is reproducible. In another aspect, the biodegradation, bioresorption, or bioerosion of implants described herein occurs contemporaneously with the ingrowth of native cells and or tissue.

In another embodiment, a process for modifying the surface of an implant to form a nano-sized implant is described herein. The process comprises the step of contacting a polymer surface with a reagent capable of breaking bonds in the polymeric molecules.

In another embodiment of the nano-structured implants described herein, the nano-structural features are formed on the surface of such polymers by a molding process. It is appreciated that this molding process may be less likely to alter the elemental and or functional group composition of the polymer than chemical treatment or chemical etching techniques or processes.

In one aspect, a molding process for forming nano-sized polymer films is described herein. The molding process comprises the step of contacting a solution of a polymer with a molding surface having thereon nano-sized structures, features, and or textures. The molding surface may be any material that has thereon such a surface, or may be prepared from such materials, and includes other polymeric materials, metals, ceramics, and natural components, such as tissues, including soft tissues.

Figure 1:
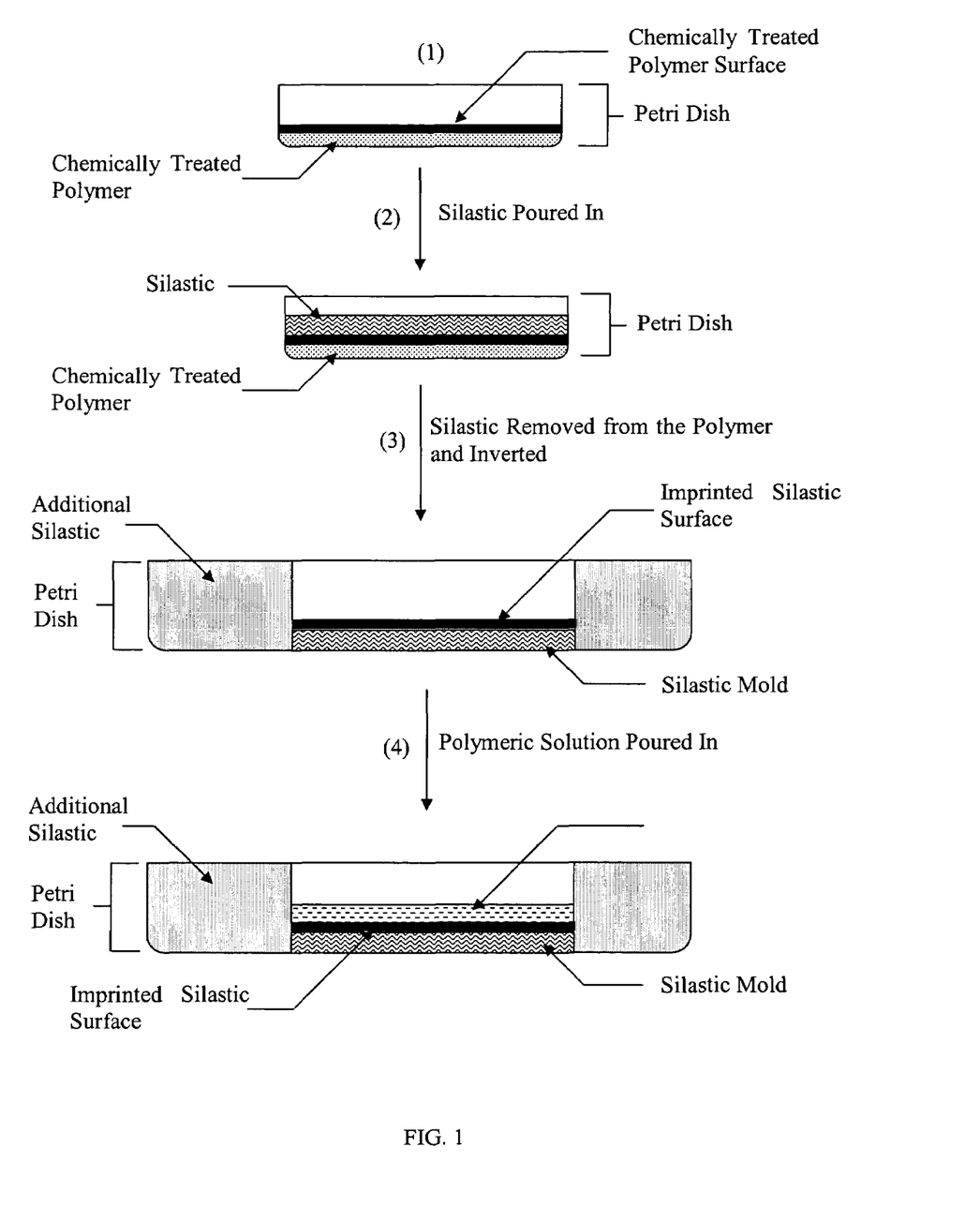
FIG. 1 shows a schematic diagram of a molding process used to cast polymer films having nono-sized features or textures.

In one aspect, the molding surface is a silastic polymer, or other silicone elastomer. In another aspect, the molding surface is a silastic polymer having nano-sized structures, features, and or textures that are formed from a polymeric material described herein, such as a chemically treated polymeric material. In this latter aspect the siliastic molding surface is prepared by contacting siliastic with a polymer that has been chemically treated to generate a nano-sized surface thereon. An illustrative process for preparing a molding material and using such a molding material to fabricate polymeric materials having nano-sized surfaces thereon is illustrated in FIG. 1. In FIG. 1, the molding surface master, such as a chemically treated polymer surface is placed in a container, such as a petri dish (step 1). A solution of silastic, or other polymer is placed in contact with the master, and allowed to cure (step 2). The silastic, having the imprint of the nano-sized surface thereon is removed and placed in an apparatus, or in another implant container, either of which can serve as a mold (step 3). The polymer to be molded is placed in contact with the silastic mold, usually as a solution, which is subsequently cured, and a duplicate of the chemically treated polymer in step 1 having the nano-sized surface is made (step 4). This process allows the reproducible fabrication of nano-sized polymers. The polymeric materials, surfaces, and implants that are prepared by such processes are contemplated to fall within the invention as described herein.

In another embodiment, a method of treating a soft tissue injury or insult, such as a bladder injury, is described herein. The method comprises the step of placing an implant described herein into a site on the soft tissue that is in need of repair. For example, methods of repairing the bladder using implants are generally described in Gleeson & Griffith, "The use of alloplastic biomaterials in bladder substitution," *J. Urol.* 148:1377-82 (1992); and Pariente et al., "In vitro biocompatibility assessment of naturally derive and synthetic biomaterials using normal human urothelial cells," *J. Biomed. Mater. Res.* 55(1):33-39 (2001), the disclosures of which are incorporated herein by reference. These methods, and other general methods of using implants for the repair of bladder and other soft tissues may be used to repair the bladder with the implants described herein. In one illustrative aspect, the injuries for which the methods described herein are useful include injuries to the bladder resulting from cancer and surgical procedures, such as those surgical procedures used to treat bladder cancer, including but not limited to transurethral resection, which involves removal of the transitional layer; segmental cystectomy, which involves the removal of a part of the bladder; radical cystectomy, which involves the removal of the entire bladder, and the like.

In one embodiment, the implants described herein include implants that facilitate the ingrowth of native cells or tissues into the repair site. Such ingrowth may take the form of migrating cells from surrounding tissue adhering to the implant, enhanced cellular responses, better tissue integration, promotion of cell attachment, promotion of cell proliferation, cell differentiation functions, cell migrations, cell spreading, and the like. It is appreciated that seeding the implant with cells or a population of cells may coordinate with the ingrowth mechanisms described herein.

The foregoing description of illustrative embodiments, and the variations and aspect thereof, are each intended to be illustrative of the invention claimed herein; this description should not be construed or interpreted as limiting the invention. Further, the following Examples describing exemplary embodiments are intended to be illustrative of the invention described herein; they should not be construed or interpreted as limiting the invention.

EXAMPLES

Example 1

Poly(lactic acid-glycolic acid) (PLGA)

Copolymer films of poly(lactic acid)/poly(glycolic acid) (PLGA; 50:50 wt. %; 12-16.5×10$^3$ MW; Polysciences, Inc.) were synthesized by heat-dissolving the co-polymer (0.5 g) in 8 ml CHCl$_3$. The heat-dissolving process lasted for approximately 40 minutes at about 60° C. or less. The dissolved copolymers were poured into a glass petri dish, left partially covered at room temperature overnight, and vacuum dried (at 15 inches Hg gauge pressure) at room temperature for 48 hours in a vacuum oven (15 inches Hg gauge pressure) to allow the CHCl$_3$ to evaporate. The entire petri dish was placed into de-ionized water (dH$_2$O) for approximately 1-2 hours, or until the polymer film easily came off the petri dish. Finally, polymer scaffolds (10 mm×5 mm×0.5 mm) were cut from the resulting bulk polymer film.

Example 2

Poly(ether-urethane) (PU)

Poly(ether urethane) (PU; Tecoflex, medical grade SCSOA; 90-140×10$^3$ MW; Thermedics, Inc.) films were synthesized by dissolving the polymer (1.6 g) in 30 ml of THF in a glass petri dish for approximately one hour at room temperature. The glass petri dish was covered to avoid evaporation of THF, and continuous but gentle shaking was used to dissolve the polymer pellets. The dissolved PU product was poured into a new glass petri dish and left partially covered at room temperature for 48 hours to allow the THF to evaporate. Finally, polymer scaffolds (10 mm×5 mm×0.5 mm) were cut from the resulting bulk polymer film.

Example 3

Polycaprolactone (PCL)

Polycaprolactone (PCL; 10-20×10$^3$ MW; Polysciences, Inc.) films were synthesized by dissolving (under gentle but continuous shaking) the polymer (0.5 g) in 8 ml of THF in a glass petri dish for approximately one hour at room temperature. The glass petri dish was covered to avoid evaporation of THF during the dissolving process. The dissolved PCL was poured into a new glass petri dish and left partially covered at room temperature for 24 hours to allow the THF to evaporate. Finally, polymer scaffolds (10 mm×5 mm×0.5 mm) were cut from the resulting bulk polymer film.

Example 4

Etched Glass Coverslips

Borosilicate glass coverslips were degreased in acetone for 10 minutes, sonicated in acetone for 10 minutes, degreased in 70% ethanol for 10 minutes, and sonicated in 70% ethanol for 10 minutes. The samples were rinsed in $dH_2O$, etched in I N NaOH (Fisher Scientific) for 1 hour, and rinsed thoroughly (at least six times) in $dH_2O$. The glass coverslips were then dried in a oven at 70° C., sterilized by autoclaving for 30 minutes at 124° C., and dried in a oven at 70° C. for 20 minutes. The resulting sterile etched glass coverslips were used as reference substrates in the cell adhesion and proliferation experiments.

Example 5

Scanning Electron Microscopy

The topography of PLGA, PU, and PCL films was evaluated by scanning electron microscopy; such techniques are generally described by Webster et al., "Osteoblast adhesion on nanophase ceramics," *Biomaterials* 20:1221-1227 (1999), the disclosure of which is incorporated herein by reference, using a JEOL JSM-840 scanning electron microscope (JEOL USA, Inc., Peabody, Mass.). Samples were sputter-coated in gold-palladium in the presence of argon gas at room temperature, and visualized at low (250× or 500×), medium (1000×), and high (5000×) magnifications at an accelerating voltage at 5 kV. The surface feature dimensions of each substrate were measured from the SEM images using Adobe Photoshop (Adobe Systems, Inc.) imaging software; feature-dimensions were reported as ranges and were determined by averaging five different measurements per substrate.

Example 6

Atomic Force Microscopy

Polymeric films of PGLA and PU were analyzed for surface area and surface roughness changes using a NanoScope IIIa Atomic Force Microscope (MM; Digital Instruments Inc., Santa Barbara, Calif.). Height images of each sample were captured in the ambient air at 15-20% humidity at a tapping frequency of approximately 300 kHz, and a frequency near the resonance of the cantilever. The scan field of view was 5 μm×5 μm using a scanning rate of 1 Hz and 256 scanning lines. The resulting height images were analyzed using NanoScope imaging software (version 4.31, Digital Instruments, Inc.).

Z values (or heights), which increased with reducing polymer surface feature dimensions, were used in calculating the substrate surface area in a 25 μm² scanned area. The surface area (A) was found using the following equation:

$$A = l \cdot b$$

where l is the length traveled by the AFM tip over 256 scanning lines and b is the width of 256 scanned lines.

Root mean squared surface roughness values ($R_q$, in nm) were calculated using height information captured from the AFM scans. The imaging software used the following equation to calculate surface roughness:

$$(R_q)^2 = \Sigma(Z_i - Z_{ave})^2 / N$$

where $R_q$ is the rms surface roughness (standard deviation of height), $Z_{ave}$ is the average of the Z values (or heights) within the given scanning area, $Z_i$ is the current Z value, and N was the number of sample points within the given area.

Values for surface area (μm² per unit of scanned area of 25 μm²) and rms surface roughness (nm) were averaged and recorded in each of three random fields per substrate.

Example 7

Electron Spectroscopy for Chemical Analysis

Electron Spectroscopy for Chemical Analysis (ESCA) was used to characterize the surface chemistry of untreated and treated (Example 8) polymeric substrates by measuring the photoemission of a photo impinging upon an atom in the substrate. The photon may interact with an atomic orbital electron with total transfer of photon energy to the electron, leading to electron emission from the atom. The binding of an electron in an atom is given by the following equation:

$$E_B = h\nu - KE$$

where $E_B$ is the binding energy of the electron in the atom (a function of the type of atom and is environment), hv is the energy of the X-ray source used, and KE is the kinetic energy of the emitted electron, as measured in the ESCA spectrometer. $E_B$ is expressed as a frequently in electron volts, and will vary with the type of atom. Depending on the resolution, the composition of different elements, as well as the composition of different functional groups on the surface of the substrate can be obtained. Exemplary $C_{1S}$ binding energies of some common functional groups are presented in Table 1.

TABLE 1

| Functional Group | Bonding[a] | Binding Energy (eV) |
|---|---|---|
| hydrocarbon | C—H or C—C | 285.0 |
| alcohol, ether | C—O—H or C—O—C | 286.5 |
| carbonyl | C=O | 288.0 |
| amide | N—C=O | 288.2 |
| acid, ester | O—C=O | 289.0 |

[a]The binding energies are given for the underscored atom.

Treated and untreated polymeric substrates were placed in an ultra-high vacuum environment (less than about $10^{-8}$ Torr), and exposed to a low-energy, monochromatic X-ray source, which caused emission of photoelectrons from atomic shells of the elements present on the polymer surface. The electrons were detected and counted according to the energy they possessed, and spectra with peaks corresponding to the elements on the surface were generated. High-resolution $C_{1S}$ spectra corresponding to functionalities on the surface were generated by performing a narrow scan for the carbon region; functionalities were differentiated according to the binding energy they possessed with carbon.

Spectra were acquired on a Surface Science Instruments X-Probe Spectrometer (Mountain View, Calif.), which permits analysis of the outermost 20-100 Angstroms of a sample in a nearly square area. This instrument uses a monochromatized Al x-ray source to stimulate the photoemission and affect charge neutralization with a low-energy electron flood gun. The x-ray spot size used to acquire the spectra was 800

µm. Pressure in the main chamber was less than about $5\times10^{-9}$ Torr during all acquisitions. The energy of electrons emitted from the sample was measured with a hemispherical energy analyzer operating at a pass energy of either 50 eV for a high-resolution $C_{1S}$ spectra or 150 eV for survey scans (compositions). Lower pass energies provided higher spectral resolution; higher pass energies permitted more rapid data acquisition and more accurate quantitative analysis.

The binding energy scale of the high-resolution peak fit results was adjusted to correct for charging effects. The correction was determined by setting the hydrocarbon peak of the high-resolution peak envelope to 285 eV. Data acquisition, data reduction, and spectra fitting were performed using a program developed by the Service Physics, Inc. (Bend, Oreg.).

Example 8

Chemical Treatment Polymeric Substrates

Chemically treated PLGA, PU, and PCL films with submicron through nanometer surface feature dimensions were prepared by soaking PLGA, PU, and PCL polymer films (Examples 1-3) in various concentrations of NaOH and $HNO_3$, as indicated in Table 2. After chemical treatment, all polymeric substrates were rinsed thoroughly in $dH_2O$ until the eluant reached a stable pH of 7.0. For example, 10 N $HNO_3$ treated PU samples were rinsed in $dH_2O$ for approximately 4 h. All polymer samples were then air-dried and sterilized following standard techniques. For example, PLGA films were sterilized by exposure to UV light for 1 h per side, followed by soaking overnight in 70% ethanol, as described by Conly et al., "Effects of biodegradable polymer particles on rat morrow-derived stromal osteoblasts in vitro," *Biomaterials* 19:1255-68 (1998); Ishaug-Riley et al., "Three-dimensional culture of rat calvarial osteoblasts in porous biodegradable polymers," *Biomaterials* 19:1405-12 (1998); Ishaug-Riley et al., "Human articular chrondrocyte adhesion and proliferation on synthetic biodegradable polymers films," *Biomaterials* 20:2245-56 (1999), the disclosures of which are incorporated herein by reference. PU and PCL substrates were sterilized overnight by exposure to UV light using standard techniques described herein and following the polymer manufacturers' protocol. The surface feature dimensions calculated from SEM images are given in Table 2.

TABLE 2

| Polymer | Treatment/Time[b] | Surface-Feature Dimensions | |
|---|---|---|---|
| PLGA | untreated[a] | conventional | 10-15 µm |
|  | 0.1 N NaOH/10 | small-micron | ND[c] |
|  | 5 N NaOH/30 | sub-micron | 100 nm-1 µm |
|  | 10 N NaOH/60 | nanometer | 50-100 nm |
| PU | untreated[a] | conventional | >15 µm |
|  | 0.1 N $HNO_3$/10 | sub-micron | 100 nm-1 µm |
|  | 10 N $HNO_3$/30 | nanometer | 50-100 nm |
| PCL | untreated[a] | conventional | 10-15 µm |
|  | 0.1 N NaOH/1 | sub-micron | 100 nm-1 µm |
|  | 0.1 N NaOH/10 | nanometer | 50-100 nm |

[a]Control group, conventional.
[b]Minutes.
[c]Not determined

AFM analysis of the chemically treated PLGA and PU substrates of Example 8 is presented in Table 3. Analysis also indicated that the average height of the surface features increased with increasing concentration of NaOH (for PLGA), increasing concentration of $HNO_3$ (for PU), and increasing treatment times for both polymers.

TABLE 3

| Polymer | Treatment/Time[b] | Feature Dimensions | Surface Area[c] | Surface Roughness[d] |
|---|---|---|---|---|
| PLGA | untreated[a] | conventional | 25.78 ± 0.26 | 21.80 ± 4.18 |
|  | 0.1 N NaOH/10 | small-micron | 25.33 ± 0.04 | 35.31 ± 5.92* |
|  | 5 N NaOH/30 | sub-micron | 25.67 ± 0.02 | 70.30 ± 4.56* |
|  | 10 N NaOH/60 | nanometer | 27.12 ± 0.01* | 206.14 ± 19.54** |
| PU | untreated[a] | conventional | 25.37 ± 0.16 | 16.34 ± 9.37 |
|  | 0.1 N $HNO_3$/10 | sub-micron | 25.12 ± 0.03 | 10.72 ± 2.17 |
|  | 10 N $HNO_3$/30 | nanometer | 32.73 ± 1.13* | 368.82 ± 71.24** |

[a]Conventional untreated control.
[b]Chemically treated.
[c]Mean of 3 samples, µm$^2$ per unit of scanned area (25 µm$^2$).
[d]Mean of 3 samples, nanometers.
*$p < 0.05$ compared to values for respective conventional polymer formulations.
**$p < 0.01$ compared to values for respective conventional polymer formulations.

The low-resolution ESCA analysis of chemically treated polymers are given in Table 4. These results show the presence of certain elements on the surface of various substrates. In addition, these results show the changes to the elemental composition of the substrates following various chemical treatments.

TABLE 4

| Polymer | Feature Dimensions | Element (%) | | | | |
|---|---|---|---|---|---|---|
|  |  | C | O | Si[a] | N | Sn[b] |
| PLGA | conventional | 58.2 | 35.0 | 6.8 | 0.0 | 0.0 |
|  | small-micron | 61.7 | 32.6 | 5.7 | 0.0 | 0.0 |
|  | sub-micron | 58.5 | 35.2 | 6.4 | 0.0 | 0.0 |
|  | nanometer | 64.8 | 21.6 | 13.6 | 0.0 | 0.0 |
| PU | conventional | 65.1 | 19.0 | 15.3 | 0.0 | 0.6 |
|  | sub-micron | 63.4 | 20.7 | 15.0 | 0.9 | 0.0 |
|  | nanometer | 71.6 | 19.8 | 7.8 | 0.7 | 0.0 |
| PCL | conventional | 68.5 | 22.0 | 9.5 | 0.0 | 0.0 |
|  | sub-micron | 71.9 | 22.6 | 5.5 | 0.0 | 0.0 |
|  | nanometer | 64.7 | 25.2 | 10.1 | 0.0 | 0.0 |

[a]The silicon detected in each sample was assumed to originate from the silicone-based vacuum grease used to adhere substrates to the bottom of the tissue culture dishes.
[b]The tin detected in each PU sample was assumed to originate from the catalyst generally used in the production of polyurethanes.

The high-resolution ESCA analysis of chemically treated polymers are given in Table 5. These results show the presence of certain functional groups and the nature of the chemical bonding on the surface of various substrates. In addition, these results show the changes to the functional group composition or the nature of the chemical bonding on the substrates following various chemical treatments.

TABLE 5

| Feature | | Functionality (%) | | | | |
|---|---|---|---|---|---|---|
| Polymer | Dimension[a] | C—$H_x$ | C—O | O—C=O | N—C=O | C=O |
| PLGA | conventional | 45.0 | 28.0 | 27 | 0.0 | 0.0 |
|  | small-micron | 40.0 | 30.0 | 30 | 0.0 | 0.0 |
|  | sub-micron | 43.0 | 29.0 | 28.0 | 0.0 | 0.0 |
|  | nanometer | 80.0 | 11.0 | 8.0 | 0.0 | 0.0 |
| PU | conventional[a] | 78.0 | 20.0 | 1.0 | 0.0 | 1.0 |
|  | sub-micron | 71.0 | 27.0 | 1.0 | 1.0 | 0.0 |
|  | nanometer | 59.0 | 38.0 | 1.0 | 1.0 | 0.0 |
| PCL | conventional[a] | 75.0 | 14.0 | 12.0 | 0.0 | 0.0 |
|  | sub-micron | 70.0 | 17.0 | 14.0 | 0.0 | 0.0 |
|  | nanometer | 77.0 | 13.0 | 10.0 | 0.0 | 0.0 |

[a]The designations of conventional, small-micron, sub-micron, and nanometer given for each polymer correspond to the treatment conditions presented in Table 2.

Example 9

Polymer Casting of Chemically Treated PLGA and PU Films

Chemically unmodified PLGA and PU films with conventional or nanometer surface feature dimensions were prepared using silicone elastomer cast molds as shown in FIG. 1. The mold material, Sylgard 184 Silicone Elastomer (Dow Corning), was mixed (10:1 w/w base/curing agent) by stirring for 15 minutes. Entrapped air-bubbles were removed from this mixture by applying 20-23 in-Hg pressure for approximately 10-15 minutes. The resulting solution was poured onto conventional or chemically treated nano-dimensional polymeric substrates (Examples 1-2 and 8). These molds were left partially covered at room temperature for 48 hours, or until fully cured. PLGA and PU casts were then synthesized by pouring polymer solutions (Examples 1-2) onto the molds. Following polymer cure, the resulting chemically untreated conventional and nano-dimensional polymer scaffolds (10 mm×5 mm×0.8 mm) were cut from the bulk polymer films. The surface features were analyzed by SEM, and the results are given in Table 6

TABLE 6

| Cast Polymer | Conventional Surface-Feature Dimensions[a] | Nano Surface-Feature Dimensions[b] |
|---|---|---|
| PLGA | 10-15 μm | 50-100 nm |
| PU | >15 μm | 50-100 nm |

[a]Conventional casting.
[b]Casting onto nano-structured silastic mold.

Example 10

Ovine Bladder Smooth and Muscle Cells

Cell isolation and culture. Ovine bladder smooth muscle cells were isolated from neonatal ovine bladder muscularis using techniques described by Haberstroh et al., "The effects of sustained hydrostatic pressure on select bladder smooth muscle cell functions," *J. Urol.* 162:2114-18 (1999), the disclosure of which is incorporated herein by reference. Bladder tissue was aseptically removed from animals and washed repeatedly with phosphate-buffered saline (PBS: a solution consisting of 0.1 N sodium chloride, 0.003 N potassium chloride, 0.01 N sodium biophosphate, and 0.001 N potassium biphosphate in $dH_2O$, at a pH of 7.4). After isolating the muscular layer from the bladder tissue, smooth muscle cells were processed by the tissue explant technique using Dulbecco's Modified Eagle Medium (DMEM; Hyclone).

These primary bladder smooth muscle cells were maintained in DMEM supplemented with 10% fetal bovine serum (FBS; Hyclone) and 1% penicillin/streptomycin (P/S; Hyclone) under standard cell culture conditions (a sterile, 37° C., humidified, 5% $CO_2$/95% air environment).

Upon reaching confluency, smooth muscle cell populations were rinsed with 2-3 ml PBS, passaged with 1 nil PET (0.01% ethylene glycol bis-(β-aminoethyl ether) N,N,N',N',-tetraacetic acid, 0.05% trypsin, 0.5% polyvinylpyrrolidine, 0.5% 4(-2-hydroxyethyl)-1-piperazineethanesifonic acid, and 0.9% sodium chloride in $dH_2(O)$, resuspended in DMEM supplemented with 10% FBS and 1% P/S, and cultured under standard cell culture conditions. Bladder smooth muscle cells were used between population numbers 3 through 7 in cell adhesion and proliferation experiments.

Cell characterization. The ovine bladder smooth muscle cells were characterized by the expression of α-smooth muscle actin using standard techniques. Cells at population number 2 were seeded at a cell density of 20,000 cells per well in tissue culture slide chambers (Nalgene). At near confluence, the cells were fixed with 4% paraformaldehyde, washed with PBS, soaked in cold methanol, dried, and stored at −20° C.

Staining was performed with the Multispecies Ultrastreptavidin Detection System (Signet Laboratories). Cells on glass slides were rinsed four times with Cadenza buffer (Shandon) and permeabilized with 0.2% Triton X-100 (Sigma) for 15 min. Blocking agent was applied for 30 min at room temperature, after which the cells were incubated in anti-α-smooth muscle actin (1:200 dilution; Boehringer Manheim) for 1 h. Following incubation, the cells were washed with PBS and biotinylated anti-mouse IgG (1:200 dilution; Biogenex) was added. After 1 h, the cells were washed once with PBS and treated with alkaline phosphatase labeling reagent and Fast Red (Biogenex). Following counterstaining with Gill's Hematoxylin (Sigma), coverslips were applied onto the stained cells. The expression of α-smooth muscle actin by bladder smooth muscle cells was visualized using light microscopy.

Example 11

Ovine Bladder Smooth Muscle Cell Morphology and Adhesion on Chemically Treated Substrates Bladder smooth muscle cells were enzymatically lifted from polystyrene tissue culture dishes using 1 ml of PET and resuspended in DMEM supplemented with 10% FES and 1% P/S. Cells were seeded (3,500 cells/$cm^2$) onto conventional and chemically treated small-micron, sub-micron, and nanometer polymeric substrates (Examples 1-3 and 8) or etched glass coverslips (Example 4), and were incubated under standard cell culture conditions in DMBM supplemented with 10% FBS and 1% P/S for 4 h.

At the end of each time period, non-adherent cells were removed by gentle rinsing in PBS. Cells adherent to opaque substrates were fixed with 4% formaldehyde for 10 min, stained with Hoechst 33258 (10 µg/ml in PBS; Sigma) fluorescent dye for 10 seconds, and rinsed with PBS. Cell nuclei were visualized using fluorescence microscopy (Leica DMIRB; Leica Microsystems Wetzler GmbH, Germany). Cells adherent to transparent substrates were fixed with 10% formalin, stained with Coomassie Brilliant Blue (0.1% Coomassie Brilliant Blue in 10% glacial acetic acid, 45% methanol, and 45% dH$_2$O) for 10 minutes, and rinsed with PBS. Adherent cells were visualized using light microscopy (Leica DMIRB; Leica Microsystems Wetzler GmBH, Germany). For both opaque and transparent substrates, the number of cells in each of five random fields per substrate were counted, averaged, and reported as cell density (cells/cm$^2$). All experiments were run in triplicate and were repeated a minimum of three separate times.

Smooth muscle cells adherent to nano-structured PLGA in the presence of DEME supplemented with 10% PBS and 1% P/S exhibited a well-spread morphology after 4 h. The morphology on nano-structured PLGA substrates was superior to that on conventional PLGA, and all PU and PCL substrates tested on the present study.

Chemically treated, nano-structured polymeric substrates enhanced bladder smooth muscle cell adhesion when compared to the conventional polymeric substrates or the glass coverslip control. A 171%, 104%, and 257% increase in number of adherent cells, for PLGA, PU, and PCL, respectively was observed compared to their respective conventional micron-structured controls. Bladder smooth muscle cell adhesion was statistically greater ($p<0.01$) for PLGA, PU, and PCL.

In addition, bladder smooth muscle cell adhesion was also significantly ($p<0.01$) increased on PLGA substrates with nanometer surface feature dimensions compared to their respective small-micron structured substrates. Similarly, cell adhesion was significantly ($p<0.01$) enhanced on PU and PCL polymer formulations with nanometer surface feature dimensions compared to their respective sub-micron structured substrates.

In general, it was observed that adhesion onto nano-structured PLGA and nano-structure PCL substrates were superior to adhesion on nano-structured PU substrates, as indicated by the data set forth above.

Example 12

Ovine Bladder Smooth Muscle Cell Proliferation on Chemically Treated Substrates

Bladder smooth muscle cells were enzymatically lifted from polystyrene tissue culture dishes using 1 ml of PET and resuspended in DMBM supplemented with 10% FBS and 1% P/S. Cells were seeded (3,500 cells/cm$^2$) onto conventional and chemically treated small-micron, sub-micron, and nanometer polymeric substrates (Examples 1-3 and 8) and etched glass cover slips (Example 4), and were cultured under standard cell culture conditions in DMEM supplemented with 10% PBS and 1% P/S for 1, 3, and 5 days. Similarly, bladder smooth muscle cells were seeded (3,500 cells/cm$^2$) onto chemically untreated (cast) conventional and nano-structured polymeric substrates (Examples 1-3 and 8), were cultured under standard cell culture conditions in DMEM supplemented with 10% PBS and 1% P/S for 1, 3, and 5 days. Over this 5 day time period, cell culture media was removed and replaced with fresh media at days 1 and 3 of culture.

At the end of each time period, non-adherent cells were removed by gentle rinsing in PBS. Cells adherent to opaque substrates were fixed with 4% formaldehyde for 10 minutes, stained with Hoechst 33258 (10 µg/ml in PBS; Sigma) fluorescent dye for 10 seconds, and rinsed with PBS. Cell nuclei were visualized using fluorescence microscopy (Leica DMIRB; Leica Microsystems Wetzler GmBH, Germany). Cells adherent to transparent substrates were fixed with 10% formalin, stained with Coomassie Brilliant Blue (0.1% Coomassie Brilliant Blue in 10% glacial acetic acid, 45% methanol, and 45% dH$_2$O) for 10 minutes, and rinsed with PBS. Adherent cells were visualized using light microscopy (Leica DMIRB; Leica Microsystems Wetzler GmBH, German). For both opaque and transparent substrates, the number of cells in each of five random fields per substrate were counted, averaged, and reported as cell density (cells/cm$^2$). All experiments were run in triplicate and were repeated a minimum of three separate times.

Bladder smooth muscle cell proliferation was significantly ($p<0.01$) greater on chemically treated nano-saturated PLGA, showing a 109% increase compared to conventional PLGA after 1, 3, and 5 days. Bladder smooth muscle cell proliferation on chemically treated nano-dimensional PU was equivalent to submicron structured PU, and significantly ($p=0.05$) greater, showing a 34% increase compared to conventional PU after 5 days. Bladder smooth muscle cell proliferation on chemically treated nano-dimensional PCL was significantly ($p<0.01$) greater, showing an 82% increase compared to conventional PCL after 1 day. However, on days 3 and 5, the ladder smooth muscle cell proliferation was comparable on all PCL samples.

Bladder smooth muscle cell density on nano-structured PU substrates was similar to the density on nano-structured PCL substrates, which were both lower compared to the density on nano-structured PLGA substrates. In contrast, cell density on conventional PLGA substrates was similar to density on conventional PU substrates, which were both higher compared to density on conventional PCL substrates.

Example 13

Ovine Bladder Smooth Muscle Cell Proliferation on Chemically Untreated Substrates Smooth muscle cell proliferation was significantly ($p<0.01$) increased on chemically untreated (cast), nano-structured PLGA, showing a 51% increase compared to chemically untreated (cast), conventional micron-structured PLGA after 1, 3 and 5 days. Smooth muscle cell proliferation was significantly ($p<0.05$) increased on chemically untreated (cast), nano-structured PU, showing a 114% increase compared to chemically untreated (cast), conventional micro-structured PU after 1, 3 and 5 days. Cell density on both nano-structured and conventional PLGA was higher compared to that observed on the respective PU substrates.

Example 14

Ovine Bladder Smooth Muscle Cell Morphology and Adhesion on Substrates Coated with Extracellular Matrix Components Protein coated substrates. Etched borosilicate glass coverslips (Example 4) were coated with various protein solutions in a sterile environment at room temperature. Sterile protein solutions in PBS (5 µg/ml) were made by dissolving gelatin (denatured collagen), albumin, fibronectin, vitronectin, laminin, or collagen type I, III, or IV. Separate glass coverslips were then coated overnight at room temperature with 2 ml of each protein solution. Reference substrates were etched glass coverslips coated with protein-free PBS under similar conditions. After 24 h, protein solutions were aspirated and coverslips were rinsed with PBS in a sterile environment. These substrates were maintained in PBS for up to 10 minutes, or until cell adhesion experiments were performed.

Ovine bladder smooth muscle cell morphology and adhesion on coverslips coated with or without proteins. Thirty minutes prior to cell seeding, serum free DMBM and DMEM supplemented with 10% FBS and 1% P/S were placed onto the protein coated substrates and reference substrates, respectively.

Bladder smooth muscle cells were enzymatically lifted from polystyrene tissue culture dishes using 1 ml of PET and resuspended in serum free DMEM. Cells were seeded (3,500 cells/cm$^2$) onto each substrate and incubated under standard cell culture conditions for 4 h.

At the end of each time period, non-adherent cells were removed by gentle rinsing in PBS. Cells adherent to the substrates were fixed with 10% formalin, stained with Coomassie Brilliant Blue for 10 minutes, and rinsed with PBS. Cell morphology was examined using light microscopy (Nikon Microphot-FXA; Nikon, Japan) and digital imaging (Flashbus FBG 4.2; Integral Technologies, Inc.). In addition, the number of cells in each of the five random fields per substrate were counted using light microscopy (Olympus CR2; Olympus, Germany), averaged, and reported as cell density (cells/cm$^2$). All experiments were run in triplicate and repeated a minimum of three separate times.

Bladder smooth muscle cells adherent on glass coverslips coated with collagen type IV in the presence of serum free DMEM exhibited superior spread morphology compared to those adherent on glass coverslips coated with vitronectin and collagen type III, which exhibited superior morphology to those adherent on the albumin-coated control coverslips.

In addition, collagen type IV enhanced bladder smooth muscle cell adhesion compared to the ablumin control coverslips. Cell adhesion was significantly ($p<0.05$) increased on coverslips coated with gelatin, fibronectin, vitronectin, laminin, and collagen type I, and was significantly ($p<0.01$) increased on glass coverslips coated with collagen type IV, after 4 h of incubation. The adherent cell density on glass coverslips coated with collagen type IV was 762%, 324%, 148%, 132%, 96%, 86%, and 58% higher than on glass coverslips coated with laminin, collagen type I, albumin, fibronectin, collagen type III, vitronectin, and gelatin, respectively.

What is claimed is:

1. A nano-structured synthetic implant comprising a polymeric material, said polymeric material displaying nano-sized surface features and a surface roughness of 50 nm or greater, wherein said surface features comprise a dimension having a size within the range of 25 nm to less than 100 nm.

2. The implant of claim 1 wherein the polymeric material is selected from the group consisting of polyglycolic acid, polylactic acid, poly(lactic acid-glycolic).

3. The implant of claim 1 wherein the nano-sized surface features have at least one dimension in the range from 25 nm to 50 nm. acid), poly(ether-urethane), polycaprolactone and poly(glycolide-caprolactone).

4. The implant of claim 1 wherein the polymer has a surface roughness of about 100 nm or greater.

5. The implant of claim 1 wherein the polymer has a surface area of greater than about 30 μm$^2$ per 25 μm$^2$.

6. The implant of claim 1 wherein the polymeric material is a polymeric film.

7. The implant of claim 6 wherein the polymeric material comprises a polymeric film of poly(lactic-glycolic acid) and arginine-aspartic acid peptides.

8. The implant of claim 1 wherein the polymeric material is a biodegradable polymer.

9. The implant of claim 1 wherein the polymeric material comprises a compound selected from the group consisting of poly(lactic acid-glycolic acid), poly(ether-urethane), and polycaprolactone.

10. The implant of claim 9 further comprising an extracellular matrix compound selected from the group consisting of collagen I, collagen III, collagen IV, collagen V, laminin, fibronectin, elastin, elastin-associated microfibrillar proteins, proteoglycans and arginine-aspartic acid peptides.

11. The implant of claim 10 further comprising a population of cells, said population of cells seeded on the polymer surface.

12. The implant of claim 11 wherein the cells are selected from the group consisting of smooth muscle cells, fibroblasts, urothelial cells, neutrophils, monocytes, fibroblasts, and macrophages.

13. The implant of claim 1 further comprising an extracellular matrix component of bladder smooth muscle cells.

14. The implant of claim 13 wherein the extracellular matrix component is incorporated into said implant.

15. The implant of claim 14 wherein the extracellular matrix component is selected from the group consisting of proteins, growth factors, and cytokines.

16. The implant of claim 13 wherein the extracellular matrix component is coated on the surface of said implant.

17. The implant of claim 13 wherein the extracellular matrix component is coated on the surface and incorporated into said implant.

18. The implant of claim 13 wherein the extracellular matrix component is selected from the group consisting of proteins, growth factors, and cytokines.

19. The implant of claim 13 wherein the extracellular matrix component is selected from the group consisting of collagen I, collagen III, collagen IV, collagen V, laminin, fibronectin, elastin, elastin-associated microfibrillar proteins, proteoglycans and arginine-aspartic acid peptides.

20. The implant of claim 13 wherein the extracellular matrix component is collagen IV.

21. The implant of claim 1 wherein the nano-sized surface features are formed by a molding process and have one or more dimensions in the range from 50 nm to less than 100 nm.

22. A nano-structured synthetic implant comprising a polymeric material, said polymeric material displaying nano-sized surface features and a surface roughness of 50 nm or greater, wherein the surface features are formed by chemical treatment of said polymeric material, and have one or more dimensions in the range from 50 nm to less than 100 nm.

23. The implant of claim 22 wherein the chemical treatment comprises contacting the polymer with a compound selected from the group consisting of HCl, $H_2SO_4$, $HClO_4$, $HNO_3$, $H_3PO_4$, HF, NaOH, $K_2CO_3$ and $NaHCO_3$.

24. A nano-structured synthetic implant, said implant consisting essentially of a polymeric material having a surface roughness of 50 nm to less than 100 nm and a further surface feature having a dimension in the range from 50 nm to less than 100 nm; and a population of cells.

25. A nano-structured synthetic implant comprising a polymeric material, said polymeric material comprising peaks and valleys formed on the surface of said polymeric material, wherein a dimension selected from the group consisting of peak height, valley depth, peak width at half height and valley width at half depth, is within the range of 25 nm to less than 100 nm.

26. The nano-structured synthetic implant of claim 25 wherein the peaks and valleys are randomly distributed on the surface of said implant.

27. The nano-structured synthetic implant of claim 25 wherein the peaks and valleys are uniformly distributed on the surface of said implant.

28. The nano-structured synthetic implant of claim 25 wherein two or more dimensions selected from the group consisting of peak height, valley depth, peak width at half height and valley width at half depth, are each within the range of 25 nm or less than 100 nm.

* * * * *

UNITED STATES PATENT AND TRADEMARK OFFICE
CERTIFICATE OF CORRECTION

PATENT NO. : 7,622,129 B1
APPLICATION NO. : 10/634292
DATED : November 24, 2009
INVENTOR(S) : Haberstroh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1120 days.

Signed and Sealed this

Twenty-sixth Day of October, 2010

David J. Kappos
*Director of the United States Patent and Trademark Office*